(12) United States Patent
Risvanli et al.

(10) Patent No.: US 12,426,569 B2
(45) Date of Patent: Sep. 30, 2025

(54) ELECTRICAL TEAT DIPPING

(71) Applicant: Artange Makina Elektrik Elektronik Muhendislik Insaat Madencilik Sanayi Ve Ticaret Limited Sirketi, Elazig (TR)

(72) Inventors: Ali Risvanli, Elazig (TR); Burak Tanyeri, Elazig (TR)

(73) Assignee: Fox Robotics Laboratuvar Teknoloji Hizmetleri Sanayi Limited Sirketi, Pendik/Istanbul (TR)

( * ) Notice: Subject to any disclaimer, the term of this patent is extended or adjusted under 35 U.S.C. 154(b) by 0 days.

(21) Appl. No.: 18/276,876

(22) PCT Filed: Jun. 11, 2021

(86) PCT No.: PCT/TR2021/050571
§ 371 (c)(1),
(2) Date: Aug. 10, 2023

(87) PCT Pub. No.: WO2022/173390
PCT Pub. Date: Aug. 18, 2022

(65) Prior Publication Data
US 2024/0114872 A1    Apr. 11, 2024

(51) Int. Cl.
A01J 7/04      (2006.01)
A61L 2/00      (2006.01)
A61L 2/24      (2006.01)

(52) U.S. Cl.
CPC ............... *A01J 7/04* (2013.01); *A61L 2/0088* (2013.01); *A61L 2/24* (2013.01); *A61L 2202/14* (2013.01)

(58) Field of Classification Search
CPC . A01J 7/04; A01J 7/025; A61L 2/0088; A61L 2/24; A61L 2202/14; A61D 1/02
USPC ........................................................ 119/14.18
See application file for complete search history.

(56) References Cited

U.S. PATENT DOCUMENTS

| | | | | |
|---|---|---|---|---|
| 5,314,123 A | * | 5/1994 | Miller | A61L 2/18 239/708 |
| 5,379,724 A | * | 1/1995 | Dee | A61D 1/02 119/673 |
| 7,536,975 B2 | * | 5/2009 | Denes | A61L 2/14 119/14.47 |
| 2006/0165571 A1 | * | 7/2006 | Seon | A61J 11/008 422/305 |

* cited by examiner

*Primary Examiner* — Peter M Poon
*Assistant Examiner* — Sahar Almatrahi
(74) *Attorney, Agent, or Firm* — Andrzej Malarz, Esq.

(57) ABSTRACT

A design is an apparatus for protecting dairy cows against mastitis by enabling rapid closure of the ends of the teats, which remain open for at least two hours after milking, to prevent them from being exposed to bacteria.

2 Claims, 2 Drawing Sheets

ELECTRICAL TEAT DIPPING

TECHNICAL FIELD

Figure 1:
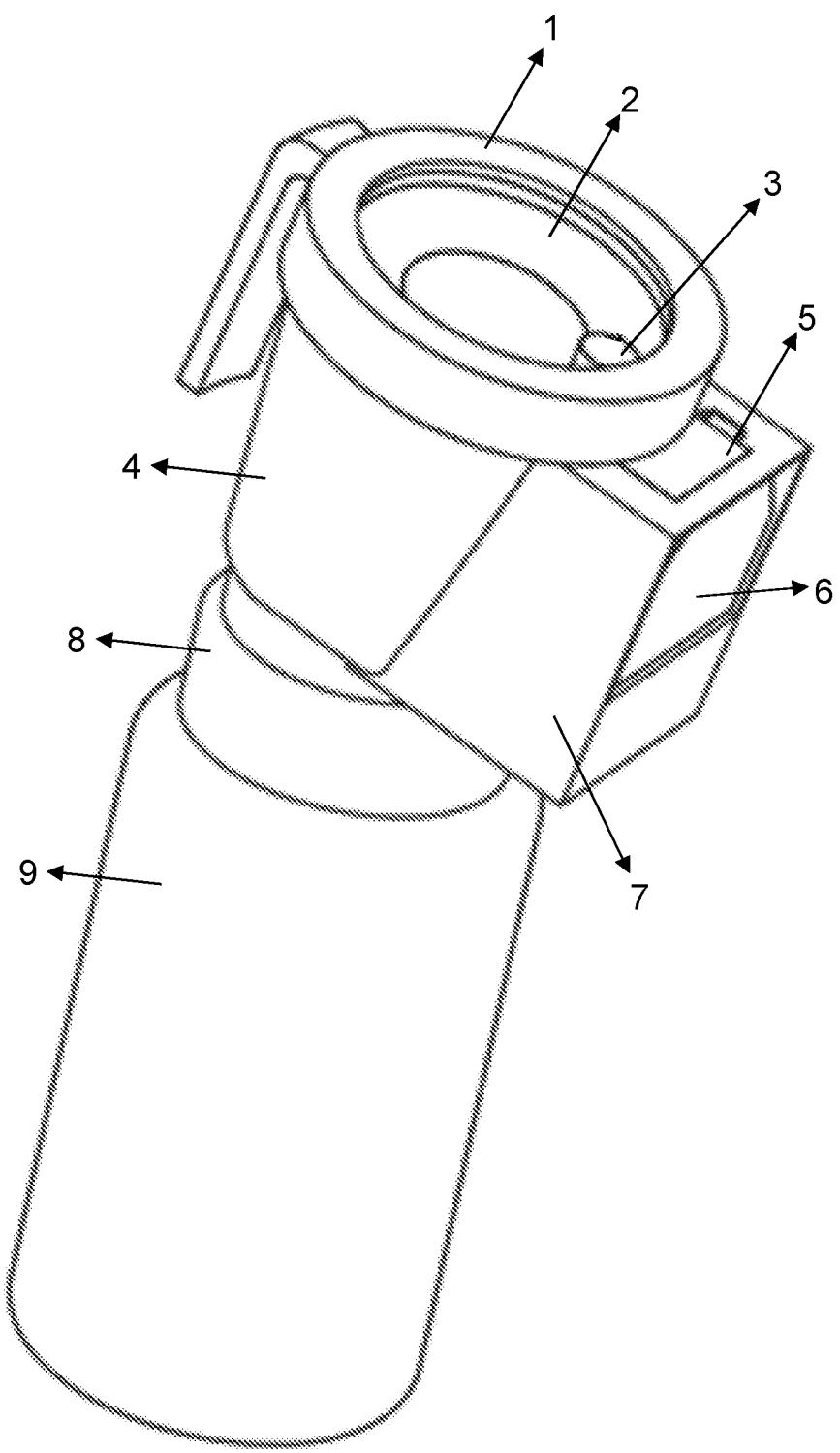

The design is an apparatus for protecting dairy cows against mastitis by enabling rapid closure of the ends of the teats, which remain open for at least two hours after milking, to prevent them from being exposed to bacteria.

BACKGROUND OF THE INVENTION

The inflammation of any structure making up the udder and surrounding the connective tissue, regardless of the cause, is called mastitis. The disease occurs as a response of the mammary gland to irritant effects, significantly affecting the udder tissue as well as the quality and quantity of milk.

Mastitis is one of the major problems in dairy cattle breeding today. Obtaining healthy milk from the udder for consumption bears importance in terms of human health. The disease causes millions of dollars of loss in the livestock economy annually, as a result of the damages it causes to both the animal and the udder. One of the main reasons why mastitis is an important condition is that the subclinical form of the disease, which progresses without any symptoms or obvious signs, is observed 20-30 times more than the clinical form. Subclinical mastitis is not easily detected by the breeders, so the disease can persist for a long time in the animal. Additionally, treatment of subclinical and clinical mastitis is both rather difficult. Persistent and recurrent cases are very common in treatment. The damage caused by the disease in the udder is seldomly reversible. Consequently, various studies have been conducted on the treatment, elimination and prevention-control of mastitis from past to present. These studies underlined the factors that play a role in the emergence of the disease and the measures to be taken. However, the disease was not eradicated due to the various factors that play a role in its etiology. In this respect, it is highly important to determine the distribution and risk factors of mastitis specific to the region in order to minimize the damages caused by the disease. Moreover, the implementation of protective measures to be taken against these determined risk factors with a regular program bears great importance.

Negative consequences of mastitis include decreased milk yield, loss of milk, decreased quality, treatment costs, veterinary services, decreased value of the animal, exclusion of animals with mastitis or surviving the disease from, as well as additional costs brought by the protective and control measures to be taken against mastitis.

Loss due to mastitis constitutes 26% of the economic burden caused by animal diseases. Also, an udder lobe infection causes a 10-12% decrease in milk yield during lactation. Again, it is suggested that milk yield in affected udder is decreased by 15-30% in some animals.

In the USA, the number of dairy cows was approximately 9.2 million in 2013 while milk production was reported as 201 billion dollars. Loss due to subclinical mastitis cases is reported as 130 dollars per cow, whereas the cost due to clinical mastitis is 367 dollars. A study in the Netherlands found that the cost associated with clinical mastitis ranged between 164-235 Euros, which varied between 17-198 Euros per cow on a country basis.

A study conducted in the Czech Republic reported that the cost of each mastitis case corresponds to a loss of 360 Euros or 950 liters of milk, whereas only a 1% increase in global mastitis cases causes an economic loss of 1.540.000 Euros.

According to the 2017 Animal Production Statistics announced by Turkey Statistical Institute on Feb. 7, 2018, there are 15 million 944 thousand cattle and 6 million 337 thousand milking cows in Turkey. Net economic losses associated with mastitis cannot be displayed since Turkey does not utilize a routine follow-up system on the incidence of mastitis. However, the economic loss associated with mastitis is estimated to be 1.25 billion per year in Turkey.

Over 140 microorganisms have been isolated in mastitis cases so far. Mastitis is constantly present in dairy herds due to reasons such as insufficient care and feeding, incorrect milking procedures, contaminated milking equipment and poor barn conditions. It is very difficult to determine the real cause of mastitis since the effects of these factors intersect.

The prevalence of mastitis due to coagulase-negative staphylococci was reported at 16.2% in the Netherlands in 1999. While, in 2004, it was 42.2% in subclinical mastitis cases, it increased from 7.3% to 14.1% in clinical mastitis cases. *Escherichia coli* and *Streptococcus uberis* are major pathogens in clinical mastitis cases in the UK. The incidence of *Streptococcus uberis* increased from 15% in 1969 to 24.5% in 2005. In New Zealand, the incidence of clinical mastitis tends to increase towards *Streptococcus uberis*, while the incidence of *Escherichia coli* is very low. While clinical mastitis agents include *Staphylococcus aureus* and *Streptococcus dysgalactiae* in Norway, *Staphylococcus aureus* ranks the first in the Netherlands, followed by *Escherichia coli* and *Streptococcus dysgalactiae*, respectively.

Predisposing factors for mastitis include anatomical shape of the udder, udder and teat wounds, lactation period of the animal, lactation number, milking type, milking interval, milking hygiene, milk yield, season and climatic conditions, race, age, barn and shelter hygiene, stress and hormonal imbalances.

Cost plays a major role in animal breeding. Success in treating animals with mastitis is very low. In this respect, it is more important to protect animals against the disease than to treat them after contracting mastitis. The udder is not an organ to be treated but an organ that needs to be protected. Numerous prevention and control measures have been developed against mastitis, which has many factors in its etiology from past to present. However, it has been reported that practices to protect udder health bring a cost to the breeder, which has recently been announced as 33$ per animal per year, reaching up to a total of 303,600,000$ annually in the United States.

The conventional teat dipping method, where the teat is dipped in the antiseptic solution, is the most effective method for protection and control against mastitis in dairy cattle breeding. However, current methods fail to provide full protection against mastitis since the teats remain open for 2 hours after the milking process. Leaving the teat canal open for at least 2 hours after milking provides a suitable environment for the entry of bacteria and viruses.

BRIEF DESCRIPTION OF THE INVENTION

The design combines electrical field stimulation at varying frequencies with the method of teat dipping to apply antiseptic on the teats within 5 ms and quickly close the teat canal. In this way, the entry of bacteria into the udder will be minimized, thus preventing udder infections in cows.

LIST OF FIGURES

FIG. 1. Assembled Perspective View

Figure 2:
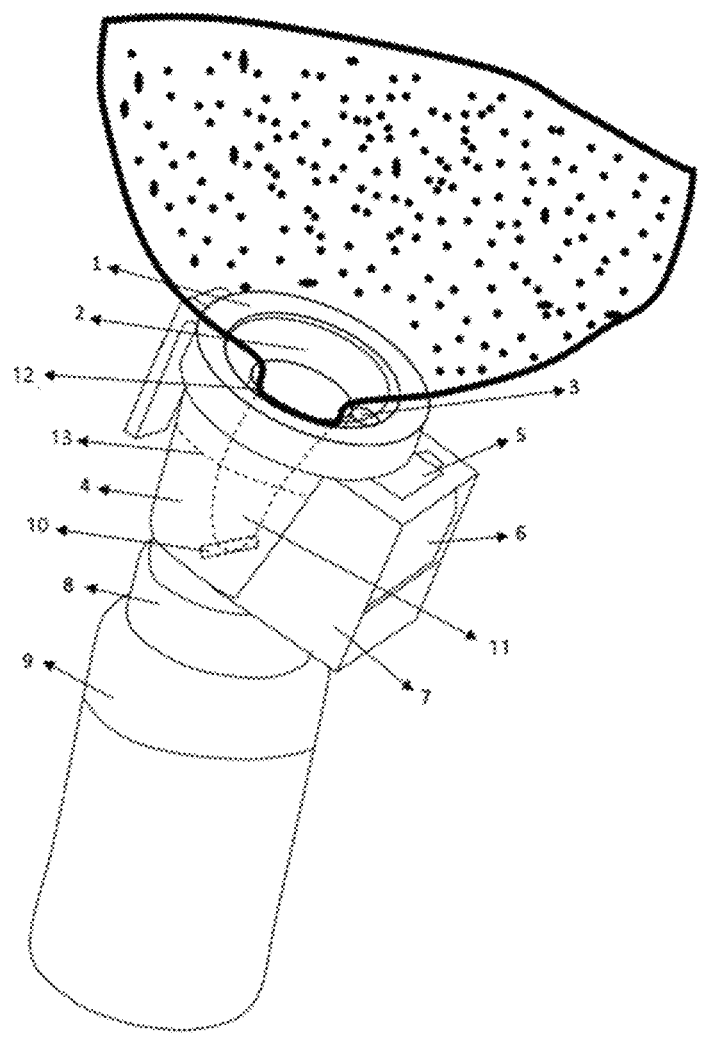

FIG. 2. Detailed perspective view of the invention.

NUMBERS IN THE FIGURES AND CORRESPONDING PARTS

1. Negative Electrode
2. Immersion Chamber
3. Overflow Channel
4. Outer Body
5. Battery Compartment
6. Electronic Card
7. Card Slot
8. Antiseptic Liquid Cover
9. Antiseptic Liquid Compartment
10. Positive Electrode
11. Teat
12. Muscle Margin
13. Antiseptic Stagnant Liquid

DETAILED DESCRIPTION OF THE INVENTION

Mastitis is the most common disease in dairy cattle. However, the disease's form of formation, various predisposing causes, and multifactorial nature, along with the problems experienced in its diagnosis and treatment) make it impossible for eradication. This is a worldwide accepted fact and the target in combating mastitis is to keep subclinical mastitis at 25-30% and clinical mastitis at 1.5%. Therefore, prevention and control methods come to the fore as the only way to reduce the damage associated with mastitis.

Prevention and control measures against mastitis can generally be grouped under 2 headings:
Prevent the occurrence of new infections
Eliminate existing infection.
Prevention of new infections includes two main factors.
1. The first is to prevent the udder from being exposed to mastitis factors. This encompasses bedding, litter management, environmental and milking hygiene practices.
2. It aims for the prevention of penetration of the agent along the teat canal and into the udder lobe.

Dipping the teat in antiseptic liquid after milking (spray applications have been used recently) is the most widely used method in protection against mastitis in dairy cattle breeding. Correct antiseptic selection and proper application reduce the rate of new udder infections by 50-90%. Available antiseptics include 0.1-1.0% iodine solutions, chlorhexidine, ammonium querternal compounds, sodium hypochlorite, hydrogen peroxide. For effective protection, teats should be immersed in antiseptic solution (teat dipping) within 1-2 seconds after the milking equipment is removed, and kept in the solution for 30 seconds. Chlorinated antiseptic solutions quickly destroy many microorganisms. However, the solution should be used within a few hours of preparation due to its relatively short half-life. Teat dipping solutions are recommended to contain substances with skin protective and softening properties such as lanolin and glycerol at a level of 10-14%.

Teat dipping stands as one of the most effective methods in this regard. The aim is to keep the teat canal, which remains open after milking, safe through the application of antiseptics with the aim to prevent microorganisms from entering the udder until it is closed. However, the teat canal remains open for about 2 hours after milking. Therefore, it is important to rapidly close the teat canal immediately after immersion to increase the effectiveness of teat dipping.

Design is comprised of the following parts and sections: a negative electrode (1), an immersion chamber (2), an overflow channel (3), an outer body (4), a battery compartment (5), an electronic card (6), a card slot (7), an antiseptic liquid cover (8), and an antiseptic fluid compartment (9). The general description of the parts is as follows: The negative electrode (1), mounted on the upper handle to determine the muscle margin to which the electrical signal will be sent and to complete the circuit by receiving the signal from the negative electrode. The lower end of immersion chamber (2), which contains antiseptic stagnant liquid (13) in which a teat (11) forming the target muscles of the milked animal is placed, holds a positive electrode (10) and allows current into the conductive antiseptic stagnant liquid (13). Antiseptic liquid compartment (9) allows the antiseptic stagnant liquid (13), the level of which is elevated via mechanical pressure, into the immersion chamber (2) through the overflow channel (3), which ensures the transfer of the antiseptic stagnant liquid (13) into the immersion chamber (2). The outer body (4) enables collaboration between the negative electrode (1), the immersion chamber (2) and the overflow channel (3) and the positive electrode as well as providing protection against external impacts. The batteries providing the energy required by the electronic card (6) are housed in the battery compartment (5) in a fixed and stable manner. The electronic card (6), which produces electronic signals and control the process, has six different patterns with adjustable current between 0.001 and 1 A, voltage between 1.5 and 50V and frequency between 1-100 Hz, with a size of 31×41×7 mm, and is located in the card slot (7) attached to the outer body (4). The antiseptic liquid compartment (9) is a unit made of soft plastic and contains an antiseptic liquid cover (8) that allows the transfer of antiseptic stagnant liquid (13) it contains into the immersion chamber (2) through the overflow channel (3) and prevents the uncontrolled discharge of the liquid.

The current study firstly presented the apparatus related to the design to apply the antiseptic solution to the teat. What separates the design from others is that it provides a signal generator via the electronic card (6), with adjustable amplitude, current and frequency, and determines the frequency of the current signals applied with the PIC control software, as well as the signal from the anode electrode, with specified output amplitude, frequency and current to be transferred into liquid, whereby the negative electrode (1) is tapped on the teat thanks to its ergonomic structure. Thus, the udder with which the liquid comes into contact is contracted by the electrical signals, thereby closing the teat canal. Electrical power becomes effective at 1.5 V voltage and 1 mA level and up to 0.5 W of power can be produced comfortably. Higher power applications result in a disturbance on the animal. Electrical conduction is provided by electrodes and antiseptics are used as intermediate conductors.

Let's use an example to show how the design works. The liquid in Antiseptic Liquid Compartment (9) is squeezed manually to increase pressure, thereby flowing into the immersion chamber (2) through the overflow channel (3). The electrical signals generated by the electronic card (6) are sent into the antiseptic liquid in the immersion chamber (2) by the anode electrode. Electrical signals pass onto the teat dipped in the liquid and onto the negative (cathode) electrode (1) tapped on the teat, thereby returning and completing the circuit. In the meantime, a contraction occurs on the muscles which cause the teat canal to close. Thus, since the teat canal returns to its pre-milking position, microorganisms that cause infection cannot enter the udder or lead to infection.

The invention claimed is:
1. An electrical apparatus for dipping teat into antiseptic characterized by;

a negative electrode, mounted on an upper handle to determine a muscle margin to which an electrical signal will be sent and to complete a circuit by receiving a signal from the negative electrode, an immersion chamber containing an antiseptic stagnant liquid in which the teat with a target muscles of a milked animal is placed, an overflow channel transferring the antiseptic stagnant liquid in antiseptic liquid compartment to the immersion chamber by elevating its level through mechanical stress, an outer body providing protection against external impacts while ensuring that a positive electrode works together with the negative electrode, the immersion chamber, and the overflow channel, a battery compartment, which houses batteries that provide the energy required by an electronic card in a fixed and stable manner, the electronic card, which produces electronic signals and control the process, with six different patterns with adjustable current between 0.001 and 1 A, voltage between 1.5 and 50V and frequency between 1-100 Hz, a card slot attached to the body where the electronic card is housed, the antiseptic liquid compartment made of soft plastic that allows the transfer of antiseptic liquid it contains into the immersion chamber through the overflow channel via manual pressure.

2. Antiseptic liquid compartment mentioned in claim 1 is characterized by its antiseptic liquid cover that prevents the discharge of the antiseptic stagnant liquid herein.

* * * * *